(12) United States Patent
Aharonov et al.

(10) Patent No.: US 9,834,821 B2
(45) Date of Patent: Dec. 5, 2017

(54) DIAGNOSIS AND PROGNOSIS OF VARIOUS TYPES OF CANCERS

(71) Applicant: ROSETTA GENOMICS LTD., Rehovot (IL)

(72) Inventors: Ranit Aharonov, Tel-Aviv (IL); Nitzan Rosenfeld, Rehovot (IL); Hila Benjamin, Kiryat Uno (IL)

(73) Assignee: ROSETTA GENOMICS LTD., Rehovot (IL)

( * ) Notice: Subject to any disclaimer, the term of this patent is extended or adjusted under 35 U.S.C. 154(b) by 24 days.

(21) Appl. No.: 14/592,111

(22) Filed: Jan. 8, 2015

(65) Prior Publication Data

US 2015/0126399 A1  May 7, 2015

Related U.S. Application Data

(62) Division of application No. 12/529,221, filed as application No. PCT/IL2008/000260 on Feb. 28, 2008, now abandoned.

(60) Provisional application No. 60/906,225, filed on Mar. 12, 2007, provisional application No. 60/904,171, filed on Mar. 1, 2007.

(51) Int. Cl.
*C12Q 1/68* (2006.01)

(52) U.S. Cl.
CPC ...... *C12Q 1/6886* (2013.01); *C12Q 2600/112* (2013.01); *C12Q 2600/158* (2013.01); *C12Q 2600/16* (2013.01); *C12Q 2600/178* (2013.01)

(58) Field of Classification Search
CPC ............ C12Q 1/6886; C12Q 2600/112; C12Q 2600/158; C12Q 2600/16; C12Q 2600/178
See application file for complete search history.

(56) References Cited

U.S. PATENT DOCUMENTS

| | | | |
|---|---|---|---|
| 5,034,506 A | 7/1991 | Summerton et al. | |
| 5,235,033 A | 8/1993 | Summerton et al. | |
| 6,506,599 B1 | 1/2003 | Yoon | |
| 7,592,441 B2 | 9/2009 | Bentwich et al. | |
| 2001/0053519 A1 | 12/2001 | Fodor et al. | |
| 2002/0012913 A1* | 1/2002 | Gunderson | C12Q 1/6809 435/6.11 |
| 2005/0272075 A1* | 12/2005 | Jacobsen | C12Q 1/6809 435/6.18 |

FOREIGN PATENT DOCUMENTS

| | | | |
|---|---|---|---|
| WO | 03029459 A2 | 4/2003 | |
| WO | 03078450 A2 | 9/2003 | |
| WO | 2005078139 A2 | 8/2005 | |

OTHER PUBLICATIONS

Nakajima et al (Cancer Genomics and Proteomics (2006) vol. 3, pp. 317-324).*
Toiyama et al (Ann Surg (2014) vol. 259, pp. 735-743).*
Lakshmipathy et al ( Stem Cells and Development (2007) vol. 16, pp. 1003-1016).*
Barad (Genome Research (2004) vol. 14, pp. 2486-2494 ans supplemental data).*
Cheung et al (Nature Genetics, 2003, vol. 33, pp. 422-425).*
Benner et al (Trends in Genetics (2001) vol. 17, pp. 414-418).*
Murakami (Oncogene (2006) vol. 25, pp. 2537-2545 and supplemental).*
Lamture (Nucleic acid Research (1994) vol. 22, p. 2121-2125).*
Barschack (International Journal of Biochemistry & cell Biology (2010) vol. 42, pp. 1355-1362).*
Karakatsanis (Molecular Carciongenesis (2013) vol. 52, pp. 297-303).*
Office Action received in the related U.S. Appl. No. 12/551,291, dated Apr. 10, 2013.
Takamizawa, et al., "Reduced Expression of the let-7 MicroRNAs in Human Lung Cancers in Association with Shortened Postoperative Survival", Cancer Research, 64, 2004, pp. 3753-3756.
Vandesompele, et al., Genome Biology, (2002), vol. 3, pp. 1-11.
Peltier, RNA (2008), vol. 14, pp. 844-852.
Puppo, et al., BJUI (2010), vol. 106, pp. 168-179.
Kirkali, et al., Urology (2005), vol. 66, pp. 4-34.
Office Action received in the parent U.S. Appl. No. 12/551,291, dated Jun. 21, 2012.
Adams, et al., Mutagenic Insertion and Chromosome Engineering Research (MICER), Nature Genetics, 2004, vol. 38, No. 8, pp. 867-871.
Endoh, et al., "Prognostic Model of Pulmonary Adenocarcinoma by Expression Profiling of Eight Genes as Determined by Quantitative Real-Time Reverse Transcriptase Polymerase Chain Reaction," J. Clin. Oncology, 2004, vol. 22, No. 5, pp. 811-819.
Shingara, RNA (2005) vol. 11, pp. 1461-1470.
Labourier, Proc Ameri Assoc Cancer Res (2005), vol. 46, abstract 4202.
Barad, et al., Genome Research (2004) vol. 14, pp. 2486-2494.
Cheung, et al., Nature Genetics, 2003, vol. 33, pp. 422-425.
Benner, et al., Trends in Genetics (2001) vol. 17, pp. 414-418.
(XP-002488899); AF480537; May 3, 2002.
(XP-002488796); AEE99464; Dec. 15, 2005.
International Search Report of the corresponding International Application PCT/IL2008/000260, dated Jul. 24, 2008.
Akao, et al., "MicroRNAs 143 and 145 are possible common onco-microRNAs in human cancers", Oncology Reports, 2006, vol. 16, pp. 845-850.
Bartel, et al., "MicroRNAs: At the Root of Plant Development?", Plant Physiology, 2003, vol. 132, pp. 709-717.
Bartel, et al., "MicroRNAs: Genomics, Biogenesis, Mechanism and Function", Cell, 2004, vol. 116, pp. 281-297.
Blaveri, et al., "Bladder cancer outcome and subtype classification by gene expression", Gene Expression in Bladder Cancer, American Association for Cancer Research, 2005. pp. 4044-0450.

(Continued)

*Primary Examiner* — Steven Pohnert
(74) *Attorney, Agent, or Firm* — Polsinelli PC; Ron Galant

(57) ABSTRACT

The present invention provides nucleic acid sequences that are used for identification, classification and diagnosis of specific types of cancers. The nucleic acid sequences can also be used for prognosis evaluation of a subject based on the expression pattern of a biological sample.

5 Claims, 12 Drawing Sheets

(56) References Cited

OTHER PUBLICATIONS

Brennecke, et al., "Principles of MicroRNA-Target Recognition", PLoS Biology, 2005, vol. 3, No. 3, pp. e85, pp. 001-0015.
Doench, et al., "Specificity of microRNA target selection in translational repression", Genes and Development, 2004, pp. 1-8.
Gottardo, et al., "Micro-RNAs profiling and bladder cancers", Proceedings of the American Association for Cancer Research, 2005, vol. 46, #6114, p. 1438.
Hofacker, et al., "Fast Folding and Comparision of RNA Secondary Structures", Monatshefte fur Chemie (Chemical Monthly), 1994, vol. 125, pp. 167-188.
Krek, et al., "Combinatorial microRNA target predictions", Nature Genetics Advanced Online Publication, Apr. 2005, pp. 1-6.
Krutzfeldt, et al., Silencing of microRNAs in vivo with 'antagromirs-, Nature, 2005, vol. 4, pp. 1-5.
Lewis, et al., "Conserved Seed Pairing, Often Flanked by Adenosines, Indicates that Thousands of Human Genes are MicroRNA Targets", Cell, 2005, vol. 120, pp. 15-20.
Lu, et al., "MicroRNA expression profiles classify human cancers", Nature, 2005, vol. 435, pp. 834-838.
Mattie, et al., "Optimized high-throughput microRNA expression profiling provides novel biomarker of clinical prostate and breast cancer biopsies", Molecular Cancer, 2006, vol. 5, No. 24, pp. doi:10.11.1186/1476-4598-5-24.
Soutschek, et al., "Therapeutic silencing of an endogenous gene by systemic administration of modified siRNAs", Nature, 2004, vol. 432, pp. 173-178.
Volinia, et al., "A microRNA expression signature of human solid tumors defines cancer gene targets", PNAS, 2006, vol. 103, No. 7, pp. 2257-2261.
Yekta, et al., "MicroRNA-Directed Cleavage of HOXB8 mRNA", Science, 2004, vol. 304, pp. 594-596.

* cited by examiner

FIG. 3

| real \ Tag | Stromal | Carcinoid |
|---|---|---|
| Stromal | 7 | 0 |
| Carcinoid | 0 | 7 |

FIG. 6

| real \ Tag | High grade | Low grade |
|---|---|---|
| High grade | 11 | 3 |
| Low grade | 0 | 6 |

DIAGNOSIS AND PROGNOSIS OF VARIOUS TYPES OF CANCERS

FIELD OF THE INVENTION

The invention relates in general to microRNA molecules associated with specific types of cancers, as well as various nucleic acid molecules relating thereto or derived therefrom.

BACKGROUND OF THE INVENTION

In recent years, microRNAs (miRs) have emerged as an important novel class of regulatory RNA, which have a profound impact on a wide array of biological processes. These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 700 known human miRs, and their number probably exceeds 800.

Classification of cancer has typically relied on the grouping of tumors based on histology, cytogenetics, immunohistochemistry, and known biological behavior. The pathologic diagnosis used to classify the tumor taken together with the stage of the cancer is then used to predict prognosis and direct therapy. However, current methods of cancer classification and staging are not completely reliable.

The treatment of bladder carcinoma is dictated by several factors. The most clinically significant prognostic parameters for tumor recurrence and invasion of bladder cancer are grade, stage, lymphatic invasion, tumor size, carcinoma in situ, multifocality and the rate of tumor recurrence. Of these parameters, pathological stage and tumor grade are seen as most important. However, staging errors are possible. Under-staging occurs in cases of high and intermediate stage disease, of which approximately 33% are typically under-staged and 10% are typically over-staged, respectively. An ideal prognostic factor must be reliable to direct treatment decisions in individuals.

Cytological analysis of voided urine is the most commonly used non-invasive method for detecting transitional cell carcinoma, but its utility is severely constrained by its low sensitivity. Several potential diagnostic markers for bladder cancer have been identified, including nuclear matrix protein 22, bladder tumor antigen, and telomerase. Although these markers are more sensitive than urine cytology for detecting bladder cancer, their use is limited by low specificity. Specific genetic alterations have been implicated in the molecular pathogenesis of transitional cell carcinoma, with mutations reported in cell cycle regulatory genes, oncogenes, and tumor suppressor genes. However, it has proven difficult to use these genetic alterations as diagnostic markers of bladder cancer because of their low sensitivity.

Procedures used for detecting, diagnosing, monitoring, staging, and prognosticating cancer of the small intestine are of critical importance to the outcome of the patient. Patients diagnosed with early stage cancer generally have a much greater survival rate as compared to the survival rate for patients diagnosed with distant metastasized cancers. New diagnostic methods which are more sensitive and specific for detecting cancer of the small intestine are clearly needed.

Nearly any primary tumor site can deposit metastases in the liver, since the liver filters blood from throughout the body. Most discussions related to the treatment of metastatic tumors in the liver focus on those originating from the colon. In fact, the most common cause of death from colorectal cancer is liver metastasis.

Up to 50% of liver metastases are of colorectal cancer origin, while the remainder metastasizes from a wide variety of primary cancer sites including sarcomas, breast and kidney, as well as neuroendocrine tumors.

Hepatocellular carcimoma (HCC—the liver primary tumor) may be solitary or multicentric, and it may mimic liver metastases. Furthermore hemangiomas and liver metastases are often confused in imaging methods. In general, the imaging appearances of liver metastases are non-specific, and biopsy specimens are required for histological diagnosis. Various biochemical markers have been proposed to indicate liver metastases. However, the diagnostic accuracy of tumor markers has not yet been defined.

Therefore, there is a need for a more efficient and effective method for diagnosing specific types of cancers.

SUMMARY OF THE INVENTION

The present invention provides specific nucleic acid sequences for use in the identification, classification and diagnosis of various types, grades and stages of cancers including but not limited to small intestine carcinoid tumor, small intestine stromal tumor, bladder carcinoma, hepatocellular carcimoma (HCC) and liver metastasis. The nucleic acid sequences can also be used as prognostic markers for prognostic evaluation of a subject based on their expression pattern in a biological sample.

The invention further provides a method for distinguishing between high grade bladder carcinoma and low grade bladder carcinoma, the method comprising: obtaining a biological sample from a subject; determining in said sample an expression level of nucleic acid sequences selected from the group consisting of SEQ ID NOS: 11-21 and 31-39, a fragment thereof or a sequence having at least about 80% identity thereto; whereby the differential higher expression of any of said nucleic acid sequences allows the classification of high grade bladder carcinoma. According to one embodiment said sample is a bladder sample.

The invention further provides a method for distinguishing between small intestine carcinoid tumor and small intestine stromal tumor, the method comprising: obtaining a biological sample from a subject; determining in said sample an expression level of nucleic acid sequences selected from the group consisting of SEQ ID NOS: 1-10 and 22-30, a fragment thereof or a sequence having at least about 80% identity thereto; whereby the differential higher expression of any of said nucleic acid sequences allows the classification of small intestine carcinoid tumor. According to one embodiment said sample is a small intestine sample.

The invention further provides a method for distinguishing between hepatocellular carcimoma (HCC) and liver metastasis, the method comprising: obtaining a biological sample from a subject; determining in said sample an expression level of nucleic acid sequences selected from the group consisting of SEQ ID NOS: 40-62, a fragment thereof or a sequence having at least about 80% identity thereto; whereby the differential expression of any of said nucleic acid sequences allows the classification of HCC versus liver metastasis.

According to one embodiment, said sample is a liver sample. According to another embodiment, said liver metastasis is adenocarcinoma.

According to some embodiments, said biological sample is selected from the group consisting of bodily fluid, a cell line and a tissue sample.

According to some embodiments, said sample is a fresh, frozen, fixed, wax-embedded or formalin fixed paraffin-embedded (FFPE) tissue.

According to some embodiments, the method comprises determining the expression levels of at least two nucleic acid sequences. According to some embodiments the method further comprising combining one or more expression ratios. According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array. According to certain embodiments, the nucleic acid hybridization is performed using in situ hybridization. According to other embodiments, the nucleic acid amplification method is real-time PCR (RT-PCR). According to one embodiment, said real-time PCR is quantitative real-time PCR (qRT-PCR).

The invention further provides a kit for determining the grade of bladder carcinoma said kit comprises a probe comprising a nucleic acid sequence selected from the group consisting of any one of SEQ ID NOS: 11-21, 31-39, fragments thereof, and sequences having at least about 80% identity thereto.

The invention further provides a kit for diagnosing a subject with a small intestine tumor, said kit comprising a probe comprising a nucleic acid sequence selected from the group consisting of SEQ ID NOS: 1-10 and 22-30, fragments thereof and sequences having at least about 80% identity thereto.

According to some embodiments, said small intestine tumor is small intestine carcinoid tumor or small intestine stromal tumor.

The invention further provides a kit for diagnosing a subject with hepatocellular carcimoma (HCC) or with liver metastasis, said kit comprising a probe comprising a nucleic acid sequence selected from the group consisting of SEQ ID NOS: SEQ ID NOS: 40-62, a fragment thereof and a sequence having at least about 80% identity thereto.

According to some embodiments, said kit comprises reagents for performing in situ hybridization analysis.

These and other embodiments of the present invention will become apparent in conjunction with the figures, description and claims that follow.

BRIEF DESCRIPTION OF THE DRAWINGS

FIG. 3 shows a table, summarizing the number of truly and falsely identified small intestine samples originated from stromal tumor versus carcinoid tumor. The rows indicate true labels and the columns indicate our identification of the samples according to the normalized expression level of hsa-miR-375. Samples whose hsa-miR-375 normalized expression levels were below the threshold (shown in FIGS. 1 and 2) were identified as stromal tumor, whereas samples whose hsa-miR-375 normalized expression levels were above the threshold were identified as carcinoid tumor. Sensitivity of stromal tumor detection was defined as the fraction of stromal samples that are correctly identified or "tagged" as stromal. The sensitivity of stromal tumor detection was 100% (7/7). The specificity of stromal tumor detection was defined as the fraction of non-stromal samples that are correctly identified ("tagged") as non-stromal. Specificity was 100% (7/7).

FIG. 6 shows a table, summarizing the number of truly and falsely identified bladder samples originated from high and low tumor grades. The rows indicate true labels and the columns indicate our identification of the samples according to the normalized expression level of hsa-miR-21. The sensitivity of the high grade tumor detection is 79% (11/14) and the specificity of the signal is 100% (6/6).

DETAILED DESCRIPTION OF THE INVENTION

Figure 1:
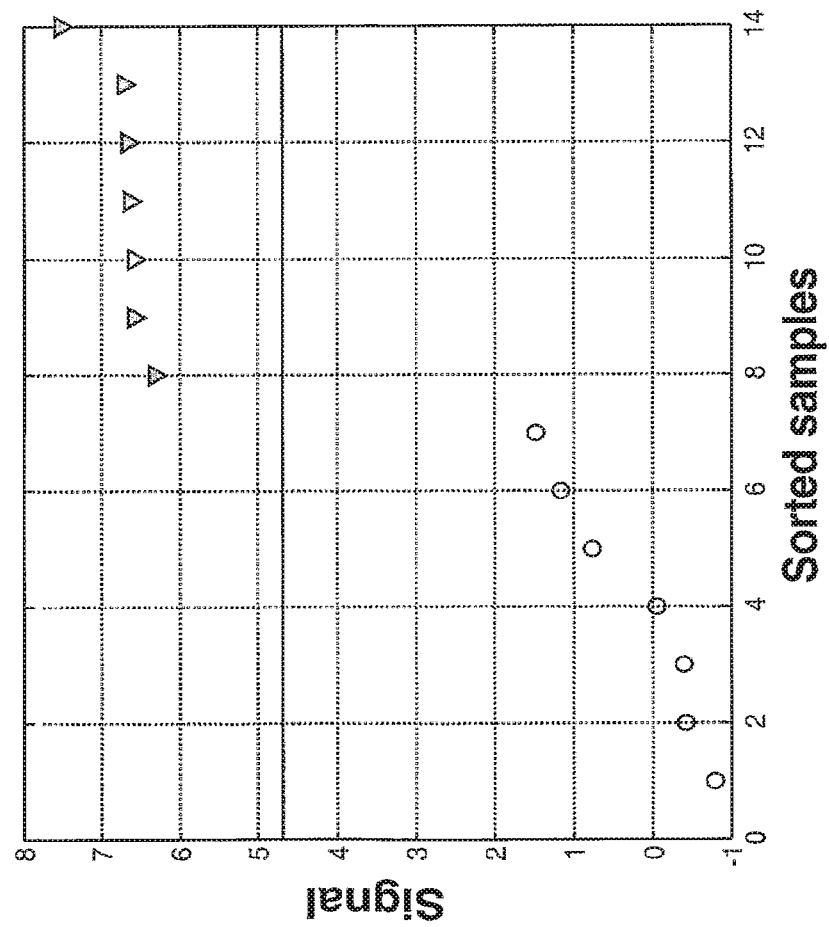
FIG. 1 shows the normalized expression level of hsa-miR-375 (SEQ ID NO: 22) in small intestine cancer samples originated from stromal tumors (circles) or carcinoid tumors (triangles). The samples are sorted according to expression level. X-axis is the sorted samples and y-axis is the normalized expression level. T-test p-value: 1.3567e-007. The horizontal line indicates a threshold of hsa-miR-375 normalized expression level, used as a criterion: a sample with hsa-miR-375 normalized expression level below this threshold will be identified as stromal tumor, whereas a sample with hsa-miR-375 normalized expression level above the threshold will be identified as carcinoid tumor.

The invention is based on the discovery that specific microRNAs (SEQ ID NOS: 1-62) can be used for the identification, diagnosis and staging of specific cancers.

The invention provides a sensitive, specific and accurate method which can be used to distinguish between small intestine carcinoid tumor and small intestine stromal tumor.

The invention further provides a method which may be used to distinguish between different grades of bladder carcinoma. The invention further provides a method which can be used to distinguish between hepatocellular carcimoma (HCC) and liver metastasis.

The methods of the present invention have high sensitivity and specificity. The possibility to distinguish between different tumor grades and origins facilitates providing the patient with the best and most suitable treatment.

The present invention provides diagnostic assays and methods, both quantitative and qualitative for detecting, diagnosing, monitoring, staging and prognosticating cancers by comparing levels of the specific microRNA molecules of the invention. Such levels are preferably measured in at least one of cells, tissues and/or bodily fluids, including determination of normal and abnormal levels. The present invention provides methods for diagnosing the presence of a specific cancer by analyzing for changes in levels of said microRNA molecules in cells, tissues or bodily fluids.

In the present invention, determining the presence of said microRNA levels in cells, tissues or bodily fluid, is particularly useful for discriminating between small intestine carcinoid tumor and small intestine stromal tumor.

The invention also provides a method of staging cancers in a subject such as different stages of bladder carcinoma.

The invention further provides a method to distinguish between hepatocellular carcimoma (HCC) and liver metastasis.

All the methods of the present invention may optionally include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Northern Blot analyses, ELISA assays and biochip.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues. Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to some embodiments, classification means determination of the type, grade, stage or origin of cancer.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Complement

"Complement" or "complementary" as used herein may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Detection

"Detection" means detecting the presence of a component in a sample. Detection may also mean detecting the absence of a component. Detection may also mean measuring the level of a component, either quantitatively or qualitatively.

Diagnosing

"Diagnosing" refers to classifying a pathology or a symptom, determining a severity of the pathology (grade or stage), monitoring pathology progression, forecasting an outcome of a pathology and/or prospects of recovery.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Expression Ratio

"Expression ratio" as used herein refers to relative expression levels of two or more nucleic acids as determined by detecting the relative expression levels of the corresponding nucleic acids in a biological sample.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distarnycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Host Cell

"Host cell" as used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

Invasive Phenotype

"Invasive phenotype" as used herein means the invasive qualities of the tested sample.

Label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Nucleic Acid

"Nucleic acid" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005) and Soutschek et al., Nature 432:173-178 (2004), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reference Value

As used herein the term "reference value" means a value that statistically correlates to a particular outcome when compared to an assay result. In preferred embodiments the reference value is determined from statistical review of studies that compare miRs expression with known clinical outcomes.

Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^1$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

"subject in need thereof" refers to an animal or human subject who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the urine (hematuria), unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, snRNA, siRNA or Piwi-interacting RNA, or a pri-miRNA, pre-miRNA, miRNA, or anti-miRNA. The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Treatment Regimen

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNAs for the identification, classification and diagnosis of specific type of cancers.

microRNA Processing

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have studied the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stein structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acid may comprise the sequence of SEQ ID NOS: 1-62 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-62 or variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-62 or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 22-49 or variants thereof.

Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-62 or variants thereof.

Binding Site of Target

The nucleic acid may also comprise a sequence of a target microRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-62.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAH (human lymphocyte) and 293 (human kidney). Host cell lines may be available from commercial services, the American Tissue Culture Collection or from published literature.

Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 10-12.

Linker Sequences

The probe may further comprise a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription Using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription Using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid. The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

A method of diagnosis is also provided. The method comprises detecting a differential expression level of cancer-associated nucleic acid in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue arrays may be performed. When comparing the fingerprints between an individual and a standard reference, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

Staging Bladder Cancer

Bladder cancers are classified based on their aggressiveness and how different they are from the surrounding bladder tissue (differentiation). They are staged and graded by physicians while diagnosing bladder cancer.

There are several different ways to stage tumors. The two most commonly used staging systems for bladder cancer are the ABCD system (the Jewett-Strong-Marshall system) and the TNM system. The ABCD system is older and uses A-B-C-D staging to classify the distinct phases or periods of bladder cancer. The system basically uses the following scale: 0, carcinoma in situ (tumor limited to the bladder mucosa (lining)); A, tumor extends through the mucosa but does not extend beyond the submucosa; B, tumor invades the muscle; C, tumor invades into the fat; and D, cancer has spread to regional lymph nodes or to distant sites. Each letter is followed by a number, for example A1, B2, etc. With the TNM system, the bladder is described by the T, the lymph nodes by the N, and distant spread by the M. Each letter is followed by a describing number, T2aN0M0. For example, Ta denotes a non-invasive papillary carcinoma; Tis denotes a carcinoma in situ; and T1 denotes a tumor invading subepithelial connective tissue.

Bladder cancers spread to the rest of the body by extending into the nearby organs, including the prostate, uterus, vagina, ureters, and rectum. Metastasis occurs through the pelvic lymph nodes, where the tumor next spreads to the liver, lungs and bones.

Grading Bladder Cancer

Bladder cancers are graded by a pathologist from the biopsy. The grade of a cancer provides information regarding how fast the cancer might be growing or how aggressive it might be. High grade cancers grow faster and spread earlier than low grade cancers. The current system of grading uses only three different grades: well-differentiated, moderately differentiated, and poorly differentiated (or Grade I, II or III). Some pathologists will use a 4-level grading system, I, II, III and IV. Either system is acceptable, and the pathologist will always note how many levels they use by declaring the cancer as a II/III or II/IV. The denominator or second number states what system they use. A well-differentiated tumor means that the cancer has more resemblance to normal bladder tissue and therefore usually does not grow or spread quickly. A poorly differentiated tumor means that the cancer does not resemble normal bladder and usually grows quickly and spreads to other tissues earlier. Moderately differentiated tumors are in the middle.

Grade, while important, has less bearing on the treatment decisions than does the stage. After the grade and stage are known, other factors also come into play before making any decision about future treatment.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, compounds for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Example 1

Experimental Procedures 1. miRdicator™ Array Platform

Custom microarrays were produced by printing DNA oligonucleotide probes to 688 miRs (miRNA) [Sanger database, version 9.1 (miRBase: microRNA sequences, targets and gene nomenclature. Griffiths-Jones S, Grocock R J, van Dongen S, Bateman A, Enright A J. NAR, 2006, 34, Database Issue, D140-D144) and additional Rosetta genomics validated and predicted miRs]. Each probe carries up to 22-nucleotide (nt) linker at the 3' end of the miRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to miRdicator™ array (1) synthetic spikes small RNA were added to the RNA before labeling to verify the labeling efficiency and (2) probes for abundant small RNA [e.g. small nuclear RNAs (U43, U49, U24, Z30, U6, U48, U44), 5.8s and 5s ribosomal RNA] were spotted on the array to verify RNA quality. The slides were blocked in a solution containing 50 mM ethanolamine, 1M Tris (pH 9.0) and 0.1% SDS for 20 min at 50° C., then thoroughly rinsed with water and spun dry.

2. Cy-Dye Labeling of microRNA for miRdicator™ Array

15 μg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and than added on top of the miRdicator™ array. Slides were hybridize 12-16 hr, followed by two washes with 1×SSC and 0.2% SDS and a final wash with 0.1×SSC.

The array was scanned using an Agilent Microarray Scanner Bundle G2565BA (resolution of 10 μM at 100% power). The data was analyzed using SpotReader software.

3. RNA Extraction

RNA was extracted from frozen or formalin fixed paraffin-embedded (FFPE) tissues.

Total RNA from frozen tissues was extracted with the miRvana miRNA isolation kit (Ambion) according to the manufacturer's instructions.

Total RNA from formalin fixed, paraffin-embedded (FFPE) tissues was extracted according to the following protocol:

1 ml Xylene (Biolab) was added to 1-2 mg tissue, incubated at 57° C. for 5 min and centrifuged for 2 mM at 10,000 g. The supernatant was removed and 1 ml Ethanol (100%) (Biolab) was added. Following centrifugation for 10 min at 10,000 g, the supernatant was discarded and the washing procedure was repeated. Following air drying for 10-15 min, 500 μl Buffer B (NaCl 10 mM, Tris pH 7.6, 500 mM, EDTA 20 mM, SDS 1%) and 5 μl proteinase K (50 mg/ml) (Sigma) were added. Following incubation at 45° C. for 16 h, inactivation of the proteinase K at 100° C. for 7 min was preformed. Following extraction with acid phenol chloroform (1:1) (Sigma) and centrifugation for 10 min at maximum speed at 4° C., the upper phase was transferred to a new tube with the addition of 3 volumes of 100% Ethanol, 0.1 volume of NaOAc (BioLab) and 8 μl glycogen (Ambion) and left over night at −20° C.

Following centrifugation at maximum speed for 40 min at 4° C., washing with 1 ml Ethanol (85%), and drying, the RNA was re-suspended in 45 μl DDW.

The RNA concentration was tested and DNase Turbo (Ambion) was added accordingly (1 μl DNase/10 μg RNA). Following Incubation for 30 min at room temperature and extraction with acid phenol chloroform, the RNA was re-suspended in 45 μl DDW. The RNA concentration was tested again and DNase Turbo (Ambion) was added accordingly (1 µl DNase/10 µg RNA). Following incubation for 30 min at room temperature and extraction with acid phenol chloroform, the RNA was re-suspended in 20 µl DDW.

4. Data Normalization

The initial data set consisted of signals measured for multiple probes for every sample. For the analysis, signals were used only for probes that were designed to measure the expression levels of known or validated human microRNAs. Data was normalized separately for each indication relative to a reference data set that was calculated separately for each indication. Each indication consisted of two sample types between which we would like to distinguish, for example: small intestine carcinoid tumor and small intestine stromal tumor. For each indication, the reference data contained one value for each probe. The vector of numbers for the reference data set is represented by R. For a given indication, the value of the reference data set for a given probe was calculated as the mean expression of this probe in two samples, one specimen from each of the two tumor/tissue types. For example, samples from small intestine carcinoid tumor and small intestine stromal tumor were normalized relative to a reference data set, where the reference value for each probe was the mean expression for that probe from one carcinoid sample and one stromal sample.

For each indication, the signals of the reference data set (represented by R) were log 2 transformed, so that $R2=\log 2(R)$. For each sample, signals for all probes (represented by S) were log 2 transformed, so that $S2=\log 2(S)$. A $2^{nd}$ degree polynomial, represented by F, was found for each sample so as to provide the best fit between the sample data and the reference data, such that $R2=F(S2)$. In this process, remote data points ("outliers") are not used for calculating the polynomial F. For each probe in the sample, the normalized value V is calculated from the initial value I by transforming it with the polynomial function F, so that $V=F(I)$.

5. Statistical Analysis

The purpose of this statistical analysis was to find probes whose normalized signal levels differ significantly between the two sample sets being compared. Probes that had normalized signal levels below log 2(300) in the two sample sets were not analyzed. For each probe, we compared two groups of normalized signals obtained for two sample sets. For each probe, we calculated the p-value, which is the probability that we would obtain by chance the measured signals or a more extreme difference between the groups if the two groups of signal come from distributions with equal mean values, using the statistical un-paired two-sided t-test method. We selected microRNAs whose probes had the lowest and most significant t-test p-values. A p-value lower than 0.05 means that the probability that the two groups come from distributions with the same mean is lower than 0.05 or 5%. The two groups of signal are likely to result from distributions with different means, and the relevant microRNA is likely to be differentially expressed between the two sets of samples.

Example 2

Specific microRNAs are Able to Distinguish Between Small Intestine Carcinoid Tumor and Small Intestine Stromal Tumor The statistical analysis of the normalized miRdicator™ arrays results of small intestine carcinoid tumor versus small intestine stromal tumor are presented in Table 1. The results exhibited a significant difference in the expression pattern of several miRs, most prominent among them being hsa-miR-375 (SEQ ID NO: 22).

Figure 2:
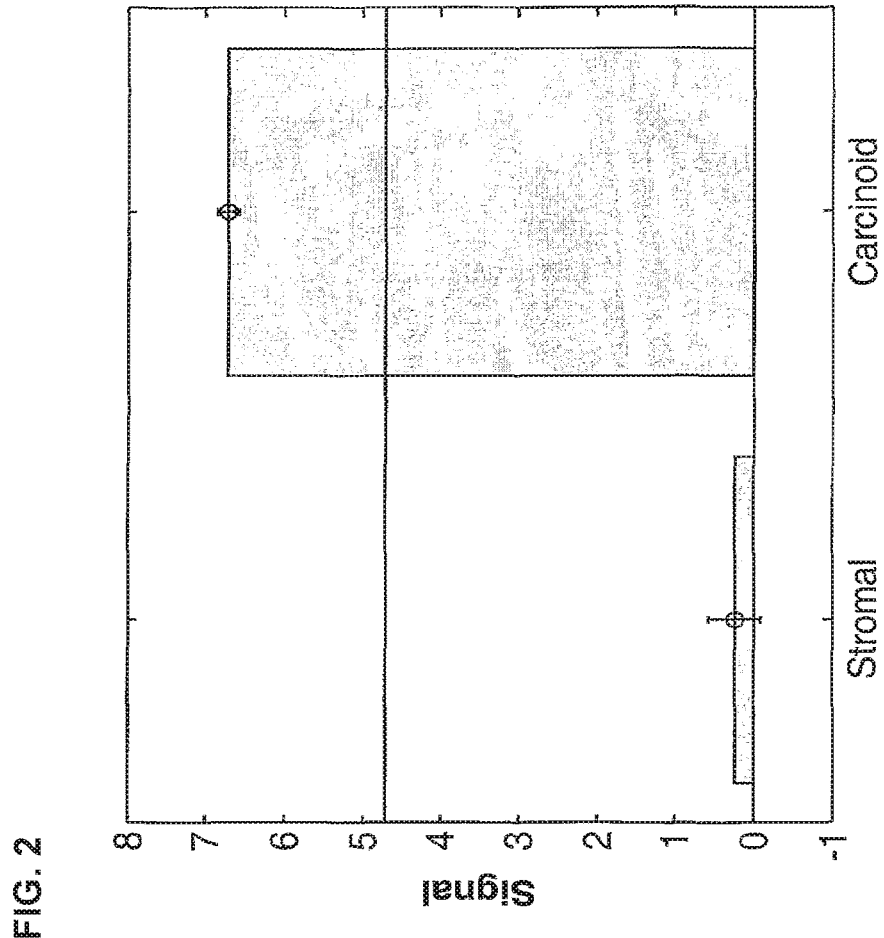
FIG. 2 shows normalized signal and standard error (STD/sqrt(n)) of the hsa-miR-375 in the two small intestine cancer sample sets: stromal tumors and carcinoid tumors.

The normalized expression levels of hsa-miR-375 were found to be higher in small intestine carcinoid tumors in comparison to small intestine stromal tumors, as measured by miRdicator™ array (FIGS. 1-3).

The sensitivity of the specific small intestine stromal tumor detection by hsa-miR-375 normalized expression is 100% (7/7) and the specificity of the signal is 100% (7/7).

TABLE 1

| miR name | HID | MID | Mean stromal (log) | Mean carcinoid (log) | Number of samples, stromal | Number of samples, carcinoid | p-value |
|---|---|---|---|---|---|---|---|
| hsa-miR-375 | 1 | 22 | 7.26 | 13.53 | 7 | 7 | 1.36E−07 |
| hsa-miR-200c | 2 | 23 | 7.9 | 12.89 | 7 | 7 | 6.11E−07 |
| hsa-miR-141 | 3 | 24 | 7.71 | 11.93 | 7 | 7 | 2.71E−06 |
| hsa-miR-194 | 4 | 25 | 8.26 | 12.89 | 7 | 7 | 3.43E−06 |
| hsa-miR-194 | 5 | 25 | 8.26 | 12.89 | 7 | 7 | 3.43E−06 |
| hsa-miR-200a | 6 | 26 | 7.9 | 11.65 | 7 | 7 | 2.07E−05 |
| hsa-miR-200b | 7 | 27 | 7.63 | 11.53 | 7 | 7 | 3.50E−05 |
| hsa-miR-193a | 8 | 28 | 9.43 | 11.06 | 7 | 7 | 3.84E−05 |
| 70_16 | 9 | 29 | 10.13 | 8.53 | 7 | 7 | 4.52E−05 |
| hsa-miR-192 | 10 | 30 | 7.93 | 11.22 | 7 | 7 | 1.07E−04 | miR name: is the miRBase registry name (release 9.1). "70_16" is not presented in the miRBase registry. It is the "mir*" of hsa-miR-455 that was cloned in Rosetta Genomics.
HID: is the SEQ ID NO of the microRNA hairpin precursor (Pre-microRNA).
MID: is the SEQ ID NO of the mature microRNA.
Mean stromal (log): is the mean of the logarithms (log) of chip signal of stormal tumor of the small intestine.
Mean carcinoid (log): is the mean of the logarithms (log) of chip normalized signal of carcinoid tumor of the small intestine.
Number of samples, stromal: is the number of samples from small intestine stromal tumor.
Number of samples, carcinoid: is the number of samples from small intestine carcinoid tumor.
p-value: is the result of unmatched t-test between samples Example 3

Specific microRNAs are Able to Distinguish Between Different Grades of Bladder Carcinoma The statistical analysis of the miRdicator™ arrays results of high grade bladder carcinoma versus low grade bladder carcinoma are presented in Table 2. The results exhibited a significant difference in the expression pattern of hsa-miR-21 (SEQ ID NO: 37).

Figure 4:
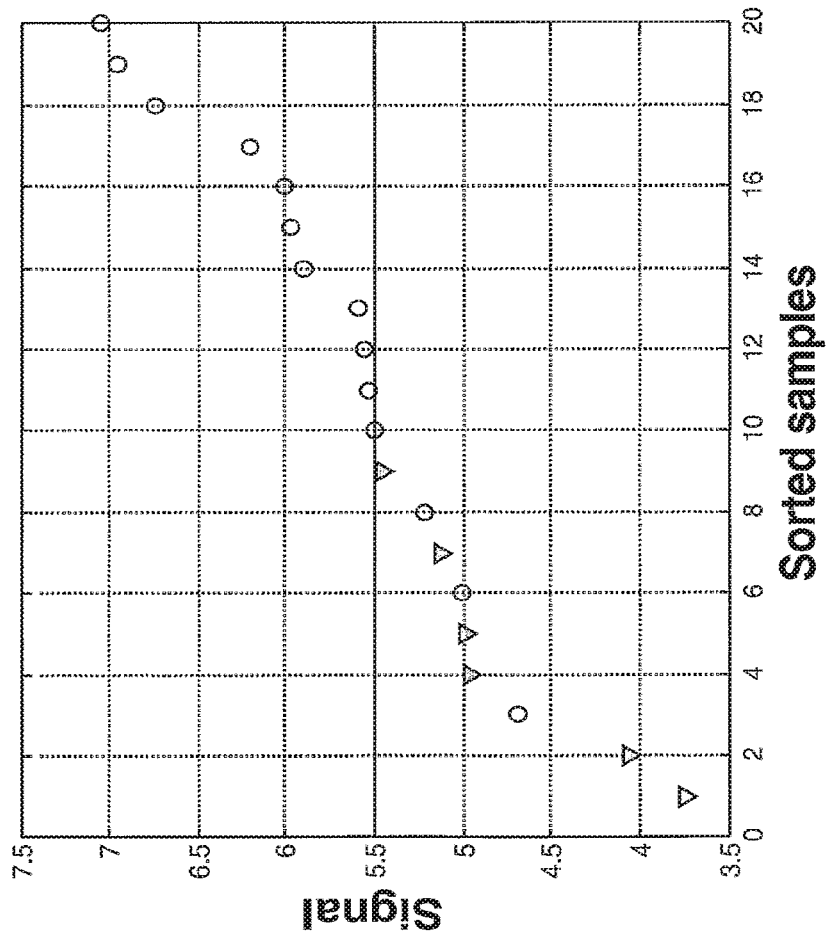
FIG. 4 shows the normalized expression level of hsa-miR-21 (SEQ ID NO: 37) in bladder samples originated from high grade (circles) or low grade tumors (triangles). The samples are sorted according to hsa-miR-21 expression level. X-axis is the sorted samples and y-axis is the normalized expression level. T-test p-value: 0.0043.
Figure 5:
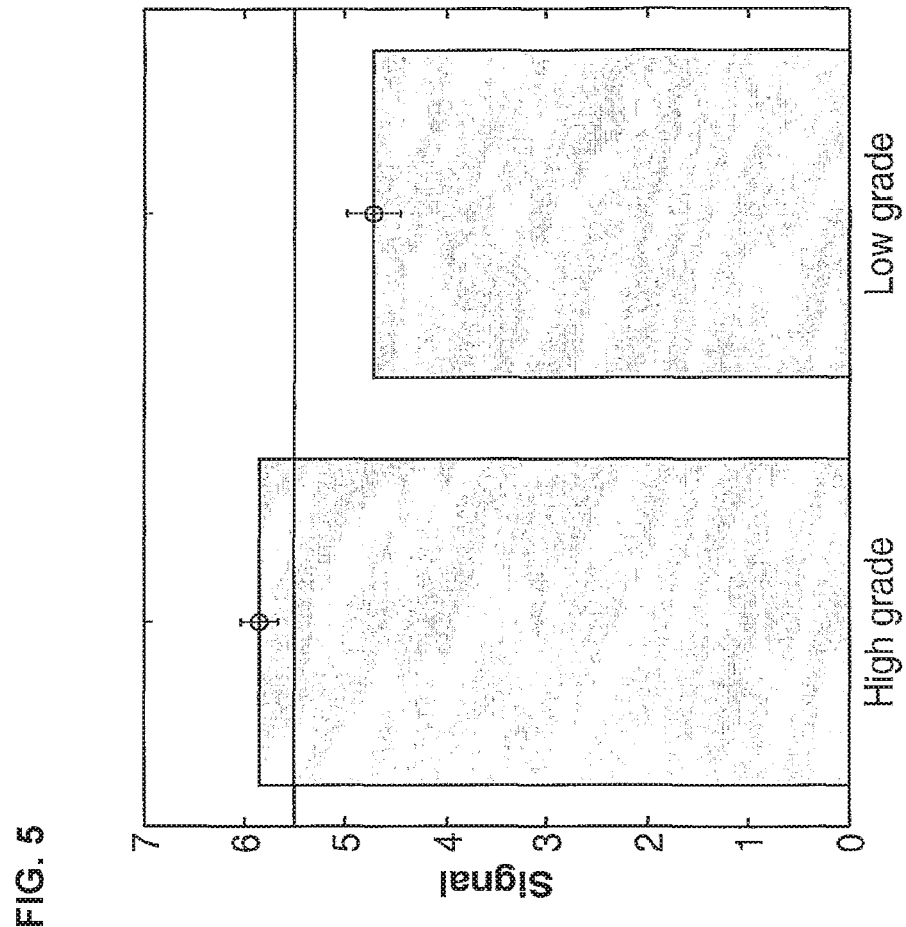
FIG. 5 shows the average normalized signal and standard error (STD/sqrt(n)) of hsa-miR-21 in the two bladder sample sets: high grade and low grade tumors.

The normalized expression levels of hsa-miR-21 were found to increase in high grade bladder carcinoma in comparison to low grade bladder carcinoma, as measured by miRdicator™ array (FIGS. 4-6).

The sensitivity of the detection by hsa-miR-21 of the high grade bladder carcinoma is 79% (11/14) and the specificity of the signal is 100% (6/6).

TABLE 2

| miR name | HID | MID | Mean high grade (log) | Mean low grade (log) | Number of samples, high grade | Number of samples, low grade | p-value |
|---|---|---|---|---|---|---|---|
| hsa-miR-191  | 11 | 31 |  9.66 | 11.86 | 14 | 6 | 4.77E−04 |
| hsa-miR-125b | 12 | 32 | 12.15 |  8.78 | 14 | 6 | 5.66E−04 |
| hsa-miR-125b | 13 | 32 | 12.15 |  8.78 | 14 | 6 | 5.66E−04 |
| hsa-miR-199a | 14 | 33 | 10.96 |  8.15 | 14 | 6 | 5.80E−04 |
| hsa-miR-199a | 15 | 33 | 10.96 |  8.15 | 14 | 6 | 5.80E−04 |
| hsa-miR-145  | 16 | 34 | 14.02 | 10.01 | 14 | 6 | 1.06E−03 |
| hsa-miR-34a  | 17 | 35 | 10    | 11.15 | 14 | 6 | 1.66E−03 |
| hsa-miR-100  | 18 | 36 |  8.43 |  6.45 | 14 | 6 | 4.22E−03 |
| hsa-miR-21   | 19 | 37 | 13.36 | 11.28 | 14 | 6 | 4.27E−03 |
| hsa-miR-149  | 20 | 38 |  7.23 |  8.32 | 14 | 6 | 4.75E−03 |
| hsa-miR-141  | 21 | 39 | 11.56 | 14.02 | 14 | 6 | 5.10E−03 | miR name: is the miRBase registry name (release 9.1).
HID: is the SEQ ID NO of the microRNA hairpin precursor (Pre-microRNA).
MID: is the SEQ ID NO of the mature microRNA.
Mean high grade (log): is the mean of the logarithms (log) of chip normalized signal of high grade (grades 2-3, 3, 3-4 and 4) bladder cancer (transitional cell carcinoma).
Mean low grade (log): is the mean of the logarithms (log) of chip signal of low grade (grades 1 and 1-2) bladder cancer (transitional cell carcinoma).
Number of samples, high grade: is the number of samples from (high grade (grades 2-3, 3, 3-4 and 4) bladder cancer (transitional cell carcinoma).
Number of samples, low grade: is the number of samples from low grade (grades 1 and 1-2) bladder cancer (transitional cell carcinoma).
p-value: is the result of unmatched t-test between samples.

Example 4

Specific microRNAs are Able to Distinguish Between Liver Metastases and Primary Liver Tumors The statistical analysis of the miRdicator™ arrays results of liver metastases vs. primary liver tumors are presented in Table 3. The results exhibited a significant difference in the expression pattern of several miRs, most prominent among them being hsa-miR-200c (SEQ ID NO: 42) and hsa-let-7a (SEQ ID NO: 49).

Figure 7:
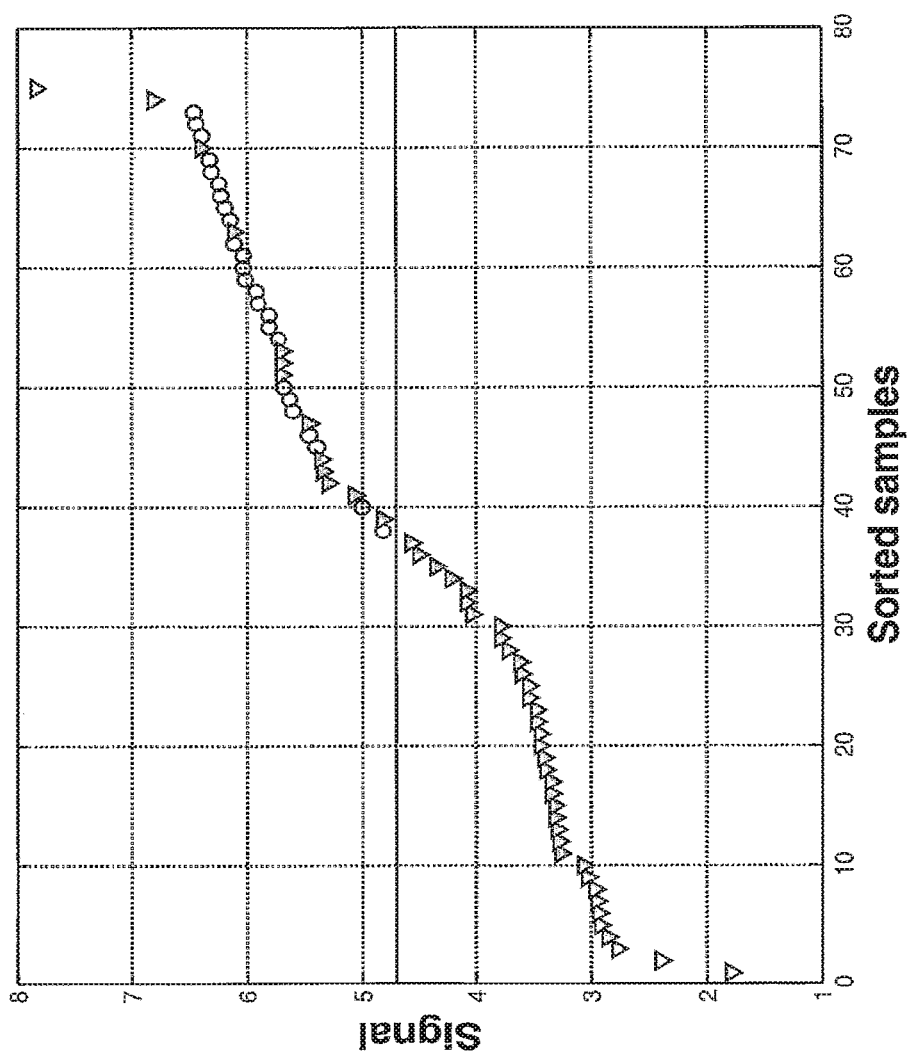
FIG. 7 shows the normalized expression level of hsa-let-7a (SEQ ID NO: 49) in liver samples originated from primary tumors (circles) or metastasis (triangles). The samples are sorted according to the expression level of hsa-let-7a. X-axis is the sorted samples and y-axis is the normalized expression level. T-test p-value: 1.7064e-011. The horizontal line indicates a threshold of hsa-let-7a normalized expression level, used as a criterion: a sample with hsa-let-7a normalized expression level below this threshold will be identified as metastasis, whereas a sample with hsa-let-7a normalized expression level above the threshold will be identified as primary.
Figure 8:
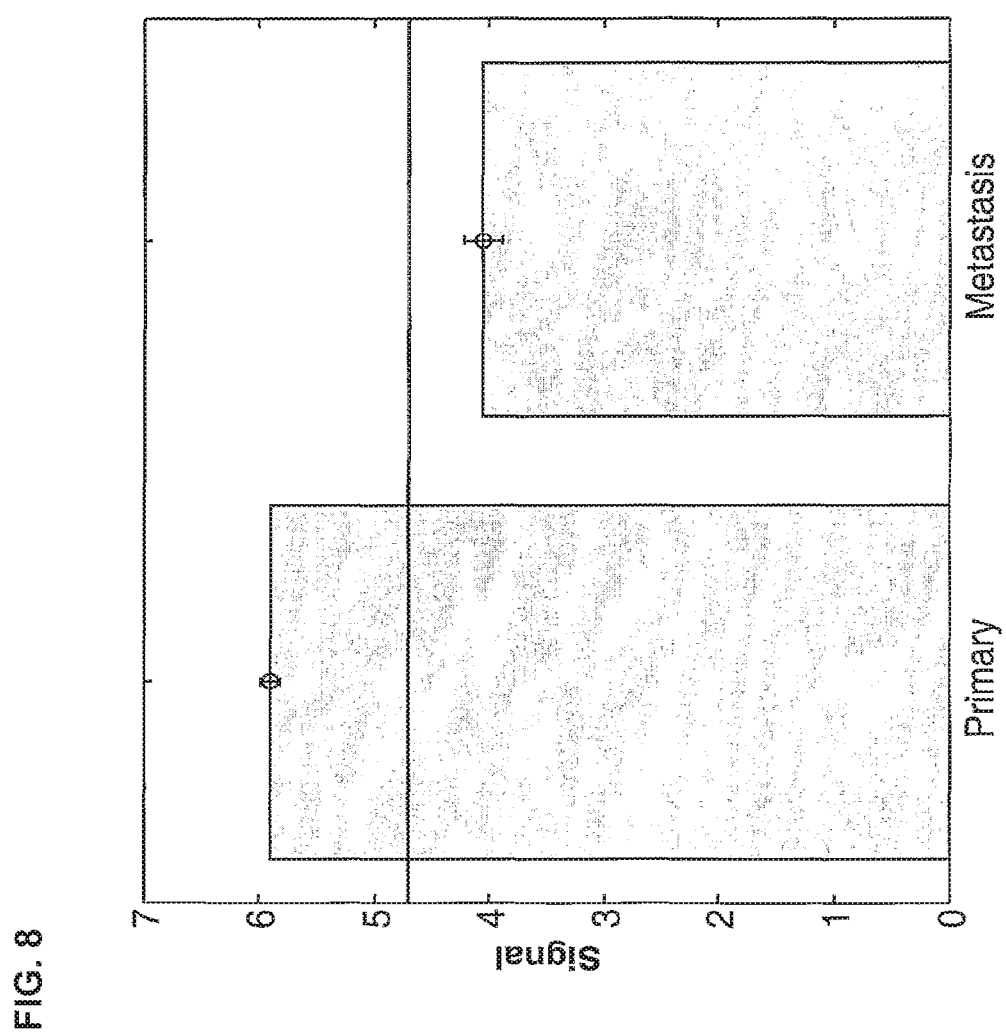
FIG. 8 shows the average normalized signal and standard error (STD/sqrt(n)) of hsa-let-7a in the two liver sample sets: primary tumors and metastasis.
Figure 9:
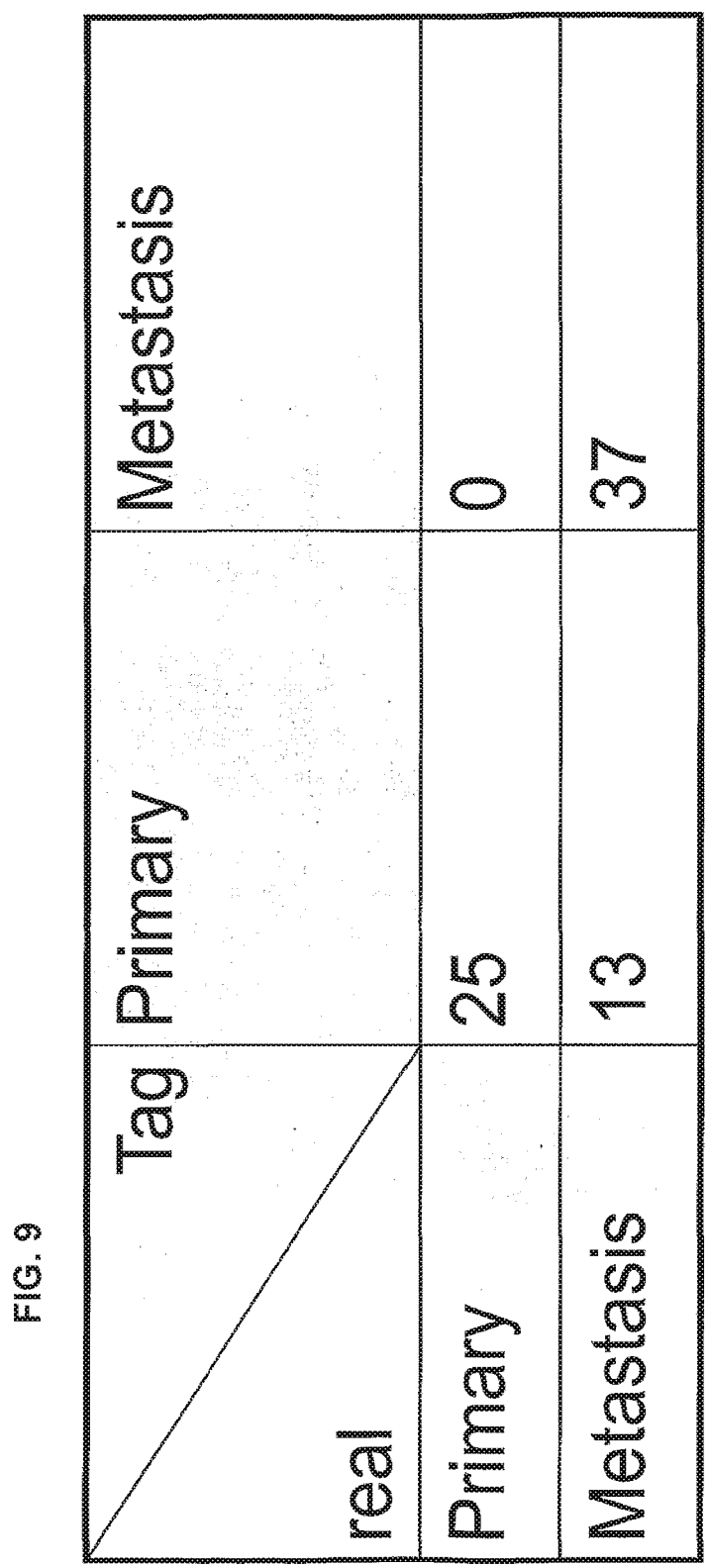
FIG. 9 shows a table, summarizing the number of truly and falsely identified primary and metastasis samples. The rows indicate true labels and the columns indicate the "tag" we assign to the samples based on our identification of the samples according to the normalized expression level of hsa-let-7a. Samples whose hsa-let-7a normalized expression levels were below the threshold (shown in FIGS. 7 and 8) were identified ("tagged") as metastases, whereas samples whose hsa-let-7a normalized expression levels were above the threshold were identified as primary. Sensitivity of metastasis detection was defined as the fraction of metastasis samples that were tagged as metastatic. Sensitivity was 74% (37/50). Specificity of metastasis detection was defined as the fraction of non-metastatic samples identified as non-metastatic. Specificity was 100% (25/25).

The normalized expression levels of hsa-let-7a were found to increase in primary liver tumors in comparison to liver metastases, as measured by miRdicator™ array (FIGS. 7-9).

The sensitivity of the liver metastasis detection by hsa-let-7a is 74% (37/50) and the specificity of the signal is 100% (25/25).

Figure 10:
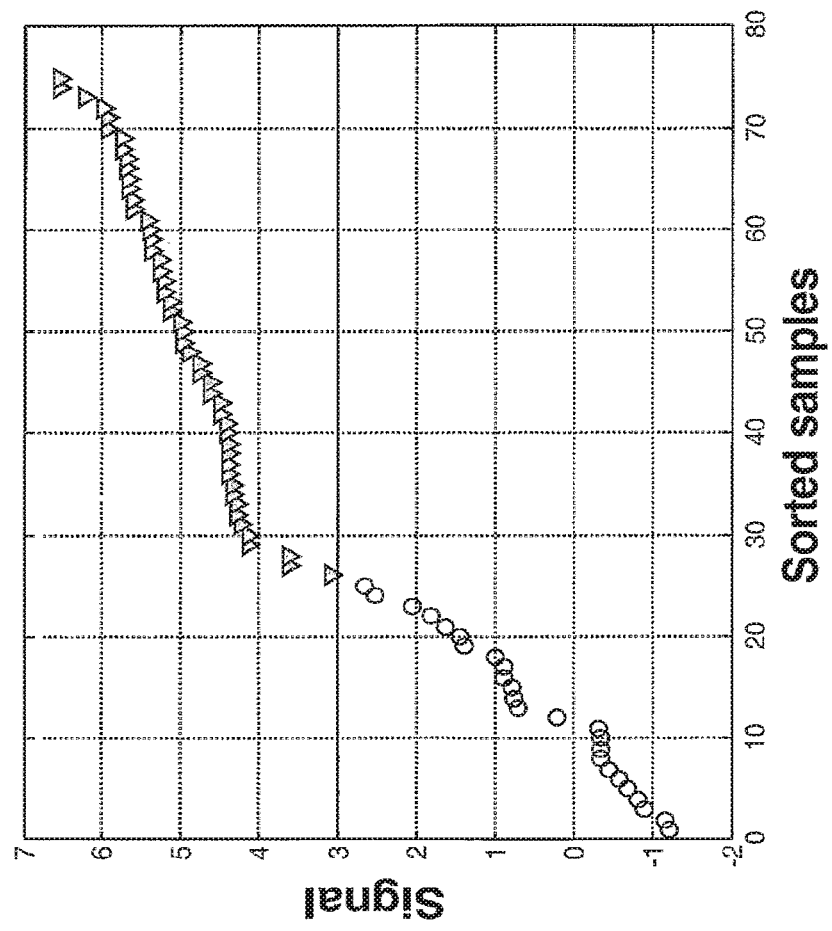
FIG. 10 shows the normalized expression level of hsa-miR-200c (SEQ ID NO: 42) in liver samples originated from primary tumors (circles) or metastasis (triangles). The samples are sorted according to the expression level of hsa-miR-200c. X-axis is the sorted samples and y-axis is the normalized expression level. T-test p-value: 50.0823e-028.
Figure 11:
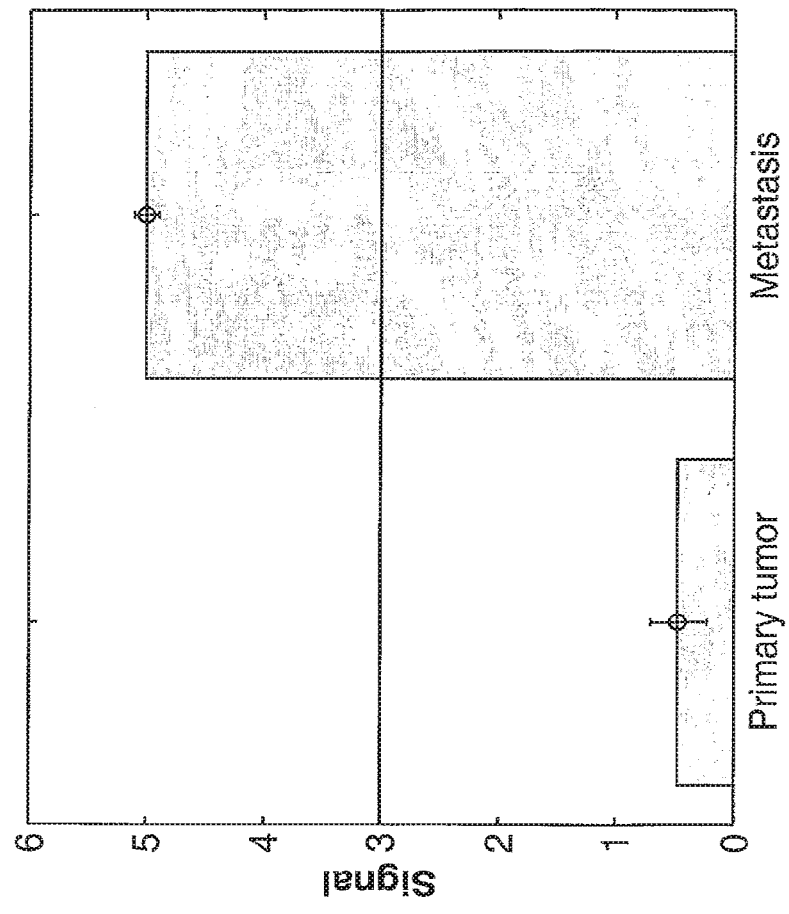
FIG. 11 shows the average normalized signal and standard error (STD/sqrt(n)) of the hsa-miR-200c in the two liver sample sets: primary tumors and metastasis.
Figure 12:
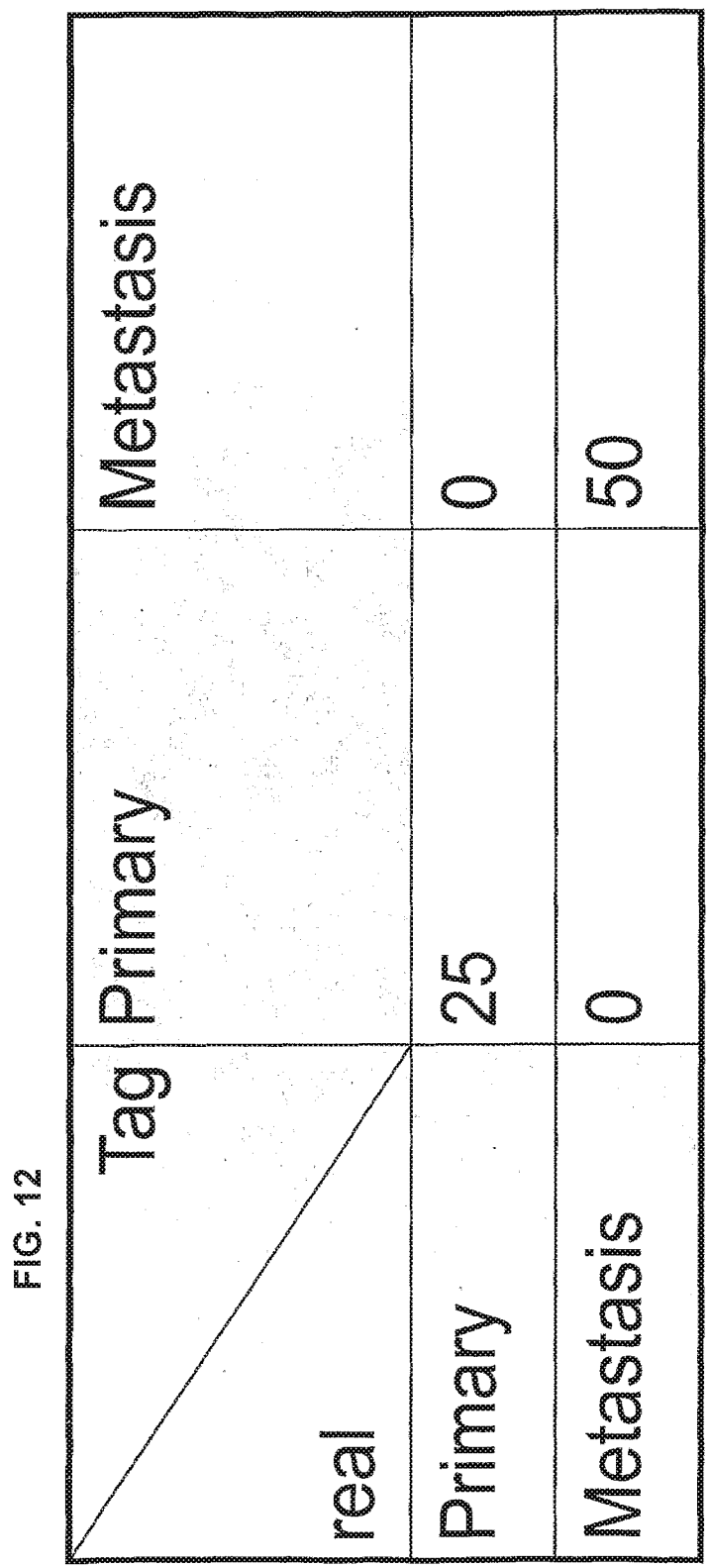
FIG. 12 shows the signal of hsa-miR-200c in liver metastasis vs. primary tumors. The signal above threshold is metastasis. The sensitivity of the metastasis detection is 100% (50/50) and the specificity of the signal is 100% (25/25).

The normalized expression levels of hsa-miR-200c were found to increase in liver metastasis in comparison to primary liver tumors (FIGS. 10-12).

The sensitivity of the metastasis detection by hsa-miR-200c is 100% (50/50) and the specificity of the signal is 100% (25/25).

TABLE 3

| miR name | HID | MID | Mean primary (log) | Mean metastasis (log) | Number of samples, primary | Number of samples, metastasis | p-value |
|---|---|---|---|---|---|---|---|
| hsa-miR-147    | 50 | 40 |  6.7  | 10.07 | 25 | 50 | 4.43E−29 |
| hsa-miR-499    | 51 | 41 |  6.32 |  9.52 | 25 | 50 | 3.68E−28 |
| hsa-miR-200c   | 52 | 42 |  7.17 | 13.02 | 25 | 50 | 5.08E−28 |
| hsa-miR-450    | 53 | 43 |  6.3  |  9.97 | 25 | 50 | 6.91E−27 |
| hsa-miR-450    | 54 | 43 |  6.3  |  9.97 | 25 | 50 | 6.91E−27 |
| hsa-miR-526b   | 55 | 44 |  6.63 | 10.81 | 25 | 50 | 6.18E−26 |
| hsa-miR-141    | 56 | 45 |  6.5  | 12.05 | 25 | 50 | 1.90E−25 |
| 43_3           | 57 | 46 |  6.83 | 10.26 | 25 | 50 | 2.88E−25 |
| hsa-miR-325    | 58 | 47 |  6.28 |  8.96 | 25 | 50 | 7.07E−25 |
| hsa-miR-493-5p | 59 | 48 |  6.68 | 10.15 | 25 | 50 | 8.53E−25 |
| hsa-let-7a     | 60 | 49 | 13.92 | 11.04 | 25 | 50 | 1.71E−11 |
| hsa-let-7a     | 61 | 49 | 13.92 | 11.04 | 25 | 50 | 1.71E−11 |
| hsa-let-7a     | 62 | 49 | 13.92 | 11.04 | 25 | 50 | 1.71E−11 | miR name: is the miRBase registry name (release 9.1). "43_3" is not presented in the miRBase registry it the "mir*" of hsa-miR-219 that is generated from hsa-mir-219-2 (and not from hsa-mir-219-1). This mir thus not in the miRBase registry was cloned in Rosetta Genomics lab.
HID: is the SEQ ID NO of the microRNA hairpin precursor (Pre-microRNA).
MID: is the SEQ ID NO of the mature microRNA.
Mean primary (log): is the mean of the logarithms (log) of chip signal of liver primary tumor.
Mean metastasis (log): is the mean of the logarithms (log) of chip signal of metastasis found in the liver.
Number of samples, primary: is the number of samples of liver primary tumor.
Number of samples, metastasis: is the number of samples of metastasis found in the liver.
p-value: is the result of unmatched t-test between samples.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of classifying a liver cancer as hepatocellular carcinoma (HCC) or liver metastasis, the method comprising: (a) providing RNA isolated from a liver sample obtained from a human subject having a liver cancer; (b) detecting in said RNA an expression level of SEQ ID NO: 42 with a nucleic acid probe consisting of a sequence complementary to SEQ ID NO: 42 and a linker of 20-27 nucleotides at the 3' end of said complementary sequence; wherein said probe is attached to a solid substrate; and wherein said expression level is normalized; (c) comparing the normalized expression level of SEQ ID NO: 42 to a reference value, wherein said reference value comprises: (i) mean normalized expression levels of SEQ ID NO: 42 in human liver cancers diagnosed as HCC, wherein increased expression of SEQ ID NO: 42 in the liver sample as compared to the reference value is indicative of liver metastasis; or (ii) mean normalized expression levels of SEQ ID NO: 42 in human liver cancers diagnosed as liver metastasis, wherein decreased expression of SEQ ID NO: 42 in the liver sample as compared to the reference value is indicative of HCC; and (d) classifying said human subject's liver cancer as HCC or liver metastasis based on said comparison.

2. The method of claim 1, wherein said liver sample is a fresh, frozen, fixed, wax-embedded or formalin fixed paraffin-embedded (FFPE) tissue.

3. The method of claim 1, wherein the expression levels are detected by a method selected from the group consisting of nucleic acid hybridization and nucleic acid amplification.

4. The method of claim 3, wherein the nucleic acid hybridization is performed using a solid-phase nucleic acid biochip array.

5. The method of claim 1, wherein the probe is attached to the solid substrate by an amine group.

* * * * *

```
                        SEQUENCE LISTING

<160> NUMBER OF SEQ ID NOS: 62

<210> SEQ ID NO 1
<211> LENGTH: 79
<212> TYPE: RNA
<213> ORGANISM: Homo sapiens

<400> SEQUENCE: 1
cgcucccgcc ccgcgacgag ccccucgcac aaaccggacc ugagcguuuu guucguucgg    60
cucgcgugag gcaggggcg                                                 79

<210> SEQ ID NO 2
<211> LENGTH: 86
<212> TYPE: RNA
<213> ORGANISM: Homo sapiens

<400> SEQUENCE: 2 gggcggggc ccucgucuua cccagcagug uuugggugcg guugggaguc ucuaauacug     60
ccggguaaug auggaggccc cugucc                                         86

<210> SEQ ID NO 3
<211> LENGTH: 104
<212> TYPE: RNA
<213> ORGANISM: Homo sapiens

<400> SEQUENCE: 3
gucggccggc ccugggucca ucuuccagua caguguugga uggucuaauu gugaagcucc    60
uaacacuguc ugguaaagau ggcucccggg uggguucucu cggc                    104

<210> SEQ ID NO 4
<211> LENGTH: 83
<212> TYPE: RNA
<213> ORGANISM: Homo sapiens

<400> SEQUENCE: 4
ugguguuauc aaguguaaca gcaacuccau guggacugug uaccaauuuc caguggagau    60
gcuguuacuu uugaugguua cca                                            83

<210> SEQ ID NO 5
<211> LENGTH: 88
<212> TYPE: RNA
<213> ORGANISM: Homo sapiens

<400> SEQUENCE: 5
auugguuccc gccccugua acagcaacuc cauguggaag ugcccacugg uuccaguggg     60
gcugcuguua ucugggcga gggccagu                                        88

<210> SEQ ID NO 6
<211> LENGTH: 90
```

```
<212> TYPE: RNA
<213> ORGANISM: Homo sapiens

<400> SEQUENCE: 6
ccgggccccu gugagcaucu uaccggacag ugcuggauuu cccagcuuga cucuaacacu    60
gucugguaac gauguucaaa ggugacccgc                                    90

<210> SEQ ID NO 7
<211> LENGTH: 95
<212> TYPE: RNA
<213> ORGANISM: Homo sapiens

<400> SEQUENCE: 7
ccagcucggg cagccguggc caucuuacug ggcagcauug gauggaguca ggucucuaau    60
acugccuggu aaugaugacg gcggagcccu gcacg                              95

<210> SEQ ID NO 8
<211> LENGTH: 88
<212> TYPE: RNA
<213> ORGANISM: Homo sapiens

<400> SEQUENCE: 8
cgaggauggg agcugagggc ugggucuuug cgggcgagau gagggugucg gaucaacugg    60
ccuacaaagu cccaguucuc ggccccg                                       88

<210> SEQ ID NO 9
<211> LENGTH: 96
<212> TYPE: RNA
<213> ORGANISM: Homo sapiens

<400> SEQUENCE: 9
ucccuggcgu gagggauugu gccuuuggac uacaucgugg aagccagcac caugcaguccc   60 augggcauau acacuugccu caaggccuau gucauc                             96

<210> SEQ ID NO 10
<211> LENGTH: 110
<212> TYPE: RNA
<213> ORGANISM: Homo sapiens

<400> SEQUENCE: 10
gccgagaccg agugcacagg gcucugaccu augaauugac agccagugcu cucgucuccc    60
cucuggcugc caauuccaua ggucacaggu auguucgccu caaugccagc               110

<210> SEQ ID NO 11
<211> LENGTH: 92
<212> TYPE: RNA
<213> ORGANISM: Homo sapiens

<400> SEQUENCE: 11
cggcuggaca gcgggcaacg gaaucccaaa agcagcuguu gucccagag cauuccagcu     60 gcgcuuggau uucgucccu gcucuccugc cu                                  92

<210> SEQ ID NO 12
<211> LENGTH: 97
<212> TYPE: RNA
<213> ORGANISM: Homo sapiens

<400> SEQUENCE: 12
uguugcgcuc cucucagucc cugagacccu aacuugugau guuuaccguu uaaauccacg    60
```

```
gguuaggcuc uugggagcug cgagucgugc uuuugca                                97
```

<210> SEQ ID NO 13
<211> LENGTH: 89
<212> TYPE: RNA
<213> ORGANISM: Homo sapiens

<400> SEQUENCE: 13

```
accagacuuu uccuaguccc ugagacccua acuugugagg uauuuuagua acaucacaag       60
ucaggcucuu gggaccuagg cggaggcga                                        89
```

<210> SEQ ID NO 14
<211> LENGTH: 83
<212> TYPE: RNA
<213> ORGANISM: Homo sapiens

<400> SEQUENCE: 14

```
ggccccgcca acccagaguu cagacuaccu guucaggagg cucucaaugu guacaguagu       60
cugcacauug guuaggcugg gcu                                              83
```

<210> SEQ ID NO 15
<211> LENGTH: 110
<212> TYPE: RNA
<213> ORGANISM: Homo sapiens

<400> SEQUENCE: 15

```
aggaagcuuc uggagauccu gcuccgucgc cccagguuc agacuaccug uucaggacaa        60
ugccguugua caguagucug cacauugguu agacugggca agggagagca                110
```

<210> SEQ ID NO 16
<211> LENGTH: 88
<212> TYPE: RNA
<213> ORGANISM: Homo sapiens

<400> SEQUENCE: 16

```
caccuugucc ucacggucca guuucccag gaaucccuua gaugcuaaga ugggauucc         60 uggaaauacu guucuugagg ucaugguu                                         88
```

<210> SEQ ID NO 17
<211> LENGTH: 110
<212> TYPE: RNA
<213> ORGANISM: Homo sapiens

<400> SEQUENCE: 17

```
ggccagcugu gaguguuucu uuggcagugu cuuagcuggu uguugugagc aauaguaagg       60
aagcaaucag caaguauacu gcccagaaag ugcugcacgu ugugggggccc               110
```

<210> SEQ ID NO 18
<211> LENGTH: 82
<212> TYPE: RNA
<213> ORGANISM: Homo sapiens

<400> SEQUENCE: 18

```
gccuguugcc acaaacccgu agauccgaac uugugguauu agccgcaca agcuuguauc        60 uauaggauaug ugucuguuag gc                                              82
```

<210> SEQ ID NO 19
<211> LENGTH: 90
<212> TYPE: RNA
<213> ORGANISM: Homo sapiens

<400> SEQUENCE: 19
guaccaccuu gucggguagc uuaucagacu gauguugacu guugaaucuc auggcaacac    60
cagucgaugg gcugucugac auuuugguau                                    90

<210> SEQ ID NO 20
<211> LENGTH: 167
<212> TYPE: RNA
<213> ORGANISM: Homo sapiens

<400> SEQUENCE: 20
cgcccgccuu gcguccagcc ugccggggc ucccaggccg gcgcccgagc ucuggcuccg     60
ugucuucacu cccgugcuug uccgaggagg gagggaggga cggggcugu gcuggggcag    120 cuggaacaac gcaggucgcc gggccggcug ggcgaguugg ccgggcg                 167

<210> SEQ ID NO 21
<211> LENGTH: 104
<212> TYPE: RNA
<213> ORGANISM: Homo sapiens

<400> SEQUENCE: 21
gucggccggc ccuggguccca ucuuccagua caguguugga uggucuaauu gugaagcucc   60
uaacacuguc ugguaaagau ggcucccggg ugggguucucu cggc                  104

<210> SEQ ID NO 22
<211> LENGTH: 20
<212> TYPE: RNA
<213> ORGANISM: Homo sapiens

<400> SEQUENCE: 22
uuuguucguu cggcucgcgu                                               20

<210> SEQ ID NO 23
<211> LENGTH: 20
<212> TYPE: RNA
<213> ORGANISM: Homo sapiens

<400> SEQUENCE: 23
uaauacugcc ggguaaugau                                               20

<210> SEQ ID NO 24
<211> LENGTH: 20
<212> TYPE: RNA
<213> ORGANISM: Homo sapiens

<400> SEQUENCE: 24
uaacacuguc ugguaaagau                                               20

<210> SEQ ID NO 25
<211> LENGTH: 20
<212> TYPE: RNA
<213> ORGANISM: Homo sapiens

<400> SEQUENCE: 25
uguaacagca acuccaugug                                               20

<210> SEQ ID NO 26
<211> LENGTH: 20
<212> TYPE: RNA
<213> ORGANISM: Homo sapiens

```
<400> SEQUENCE: 26
uaacacuguc ugguaacgau                                               20

<210> SEQ ID NO 27
<211> LENGTH: 20
<212> TYPE: RNA
<213> ORGANISM: Homo sapiens

<400> SEQUENCE: 27
uaauacugcc ugguaaugau                                               20

<210> SEQ ID NO 28
<211> LENGTH: 20
<212> TYPE: RNA
<213> ORGANISM: Homo sapiens

<400> SEQUENCE: 28
aacuggccua caaagcccca                                               20

<210> SEQ ID NO 29
<211> LENGTH: 20
<212> TYPE: RNA
<213> ORGANISM: Homo sapiens

<400> SEQUENCE: 29
gcaguccaug ggcauauaca                                               20

<210> SEQ ID NO 30
<211> LENGTH: 20
<212> TYPE: RNA
<213> ORGANISM: Homo sapiens

<400> SEQUENCE: 30
cugaccuaug aauugacagc                                               20

<210> SEQ ID NO 31
<211> LENGTH: 22
<212> TYPE: RNA
<213> ORGANISM: Homo sapiens

<400> SEQUENCE: 31
caacggaauc ccaaaagcag cu                                            22

<210> SEQ ID NO 32
<211> LENGTH: 22
<212> TYPE: RNA
<213> ORGANISM: Homo sapiens

<400> SEQUENCE: 32
ucccugagac ccuaacuugu ga                                            22

<210> SEQ ID NO 33
<211> LENGTH: 23
<212> TYPE: RNA
<213> ORGANISM: Homo sapiens

<400> SEQUENCE: 33
cccaguguuc agacuaccug uuc                                           23

<210> SEQ ID NO 34
<211> LENGTH: 24
<212> TYPE: RNA
<213> ORGANISM: Homo sapiens
```

-continued

```
<400> SEQUENCE: 34
guccaguuuu cccaggaauc ccuu                                              24

<210> SEQ ID NO 35
<211> LENGTH: 23
<212> TYPE: RNA
<213> ORGANISM: Homo sapiens

<400> SEQUENCE: 35
uggcaguguc uuagcugguu guu                                               23

<210> SEQ ID NO 36
<211> LENGTH: 22
<212> TYPE: RNA
<213> ORGANISM: Homo sapiens

<400> SEQUENCE: 36
aacccguaga uccgaacuug ug                                                22

<210> SEQ ID NO 37
<211> LENGTH: 22
<212> TYPE: RNA
<213> ORGANISM: Homo sapiens

<400> SEQUENCE: 37
uagcuuauca gacugauguu ga                                                22

<210> SEQ ID NO 38
<211> LENGTH: 22
<212> TYPE: RNA
<213> ORGANISM: Homo sapiens

<400> SEQUENCE: 38
ucuggcuccg ugucuucacu cc                                                22

<210> SEQ ID NO 39
<211> LENGTH: 22
<212> TYPE: RNA
<213> ORGANISM: Homo sapiens

<400> SEQUENCE: 39
uaacacuguc ugguaaagau gg                                                22

<210> SEQ ID NO 40
<211> LENGTH: 20
<212> TYPE: RNA
<213> ORGANISM: Homo sapiens

<400> SEQUENCE: 40
guguguggaa augcuucugc                                                   20

<210> SEQ ID NO 41
<211> LENGTH: 23
<212> TYPE: RNA
<213> ORGANISM: Homo sapiens

<400> SEQUENCE: 41
uuaagacuug cagugauguu uaa                                               23

<210> SEQ ID NO 42
<211> LENGTH: 22
<212> TYPE: RNA
```

```
<213> ORGANISM: Homo sapiens

<400> SEQUENCE: 42
uaauacugcc ggguaaugau gg                                          22

<210> SEQ ID NO 43
<211> LENGTH: 22
<212> TYPE: RNA
<213> ORGANISM: Homo sapiens

<400> SEQUENCE: 43
uuuuugcgau guguuccuaa ua                                          22

<210> SEQ ID NO 44
<211> LENGTH: 24
<212> TYPE: RNA
<213> ORGANISM: Homo sapiens

<400> SEQUENCE: 44
cucuugaggg aagcacuuuc uguu                                        24

<210> SEQ ID NO 45
<211> LENGTH: 22
<212> TYPE: RNA
<213> ORGANISM: Homo sapiens

<400> SEQUENCE: 45
uaacacuguc ugguaaagau gg                                          22

<210> SEQ ID NO 46
<211> LENGTH: 22
<212> TYPE: RNA
<213> ORGANISM: Homo sapiens

<400> SEQUENCE: 46
agaauugugg cuggacaucu gu                                          22

<210> SEQ ID NO 47
<211> LENGTH: 23
<212> TYPE: RNA
<213> ORGANISM: Homo sapiens

<400> SEQUENCE: 47
ccuaguaggu guccaguaag ugu                                         23

<210> SEQ ID NO 48
<211> LENGTH: 22
<212> TYPE: RNA
<213> ORGANISM: Homo sapiens

<400> SEQUENCE: 48
uuguacaugg uaggcuuuca uu                                          22

<210> SEQ ID NO 49
<211> LENGTH: 22
<212> TYPE: RNA
<213> ORGANISM: Homo sapiens

<400> SEQUENCE: 49
ugagguagua gguuguauag uu                                          22

<210> SEQ ID NO 50
<211> LENGTH: 72
```

```
<212> TYPE: RNA
<213> ORGANISM: Homo sapiens

<400> SEQUENCE: 50
aaucuaaaga caacauuucu gcacacacac cagacuaugg aagccagugu guggaaaugc    60
uucugcuaga uu                                                       72

<210> SEQ ID NO 51
<211> LENGTH: 122
<212> TYPE: RNA
<213> ORGANISM: Homo sapiens

<400> SEQUENCE: 51
gcccuguccc cugugccuug ggcgggcggc uguuaagacu ugcagugaug uuuaacuccu    60
cuccacguga acaucacagc aagucugugc ugcuucccgu cccuacgcug ccugggcagg   120
gu                                                                 122

<210> SEQ ID NO 52
<211> LENGTH: 68
<212> TYPE: RNA
<213> ORGANISM: Homo sapiens

<400> SEQUENCE: 52
cccucgucuu acccagcagu guuggggugc gguugggagu cucuaauacu gccggguaau    60
gauggagg                                                            68

<210> SEQ ID NO 53
<211> LENGTH: 91
<212> TYPE: RNA
<213> ORGANISM: Homo sapiens

<400> SEQUENCE: 53
aaacgauacu aaacuguuuu ugcgaugugu uccaauaug cacuauaaau auauugggaa     60
cauuuugcau guauaguuuu guaucaauau a                                  91

<210> SEQ ID NO 54
<211> LENGTH: 100
<212> TYPE: RNA
<213> ORGANISM: Homo sapiens

<400> SEQUENCE: 54
ccaaagaaag augcuaaacu auuuugcga uguuccua auauguaaua uaaauguauu       60
ggggacauuu ugcauucaua guuuguauc aauaauaugg                         100

<210> SEQ ID NO 55
<211> LENGTH: 83
<212> TYPE: RNA
<213> ORGANISM: Homo sapiens

<400> SEQUENCE: 55
ucaggcugug acccucuuga gggaagcacu uucuguuguc ugaaagaaga gaaagugcuu    60
ccuuuuagag gcuuacuguc uga                                           83

<210> SEQ ID NO 56
<211> LENGTH: 95
<212> TYPE: RNA
<213> ORGANISM: Homo sapiens

<400> SEQUENCE: 56
```
cggccggccc uggguccauc uuccaguaca guguuggaug gucuaauugu gaagcuccua    60
acacugucug guaaagaugg cucccggguug gguuc    95

<210> SEQ ID NO 57
<211> LENGTH: 97
<212> TYPE: RNA
<213> ORGANISM: Homo sapiens

<400> SEQUENCE: 57
acucaggggc uucgccacug auguccaaa cgcaauucuu guacgagucu gcggccaacc    60
gagaauugug gcuggacauc uguggcugag cuccggg    97

<210> SEQ ID NO 58
<211> LENGTH: 98
<212> TYPE: RNA
<213> ORGANISM: Homo sapiens

<400> SEQUENCE: 58
auacagugcu ugguuccuag uaggugucca guaaguguuu gugacauaau uuguuuauug    60
aggaccuccu aucaaucaag cacugugcua ggcucugg    98

<210> SEQ ID NO 59
<211> LENGTH: 89
<212> TYPE: RNA
<213> ORGANISM: Homo sapiens

<400> SEQUENCE: 59
cuggccucca gggcuuugua caugguaggc uuucauucau ucguuugcac auucggugaa    60
ggucuacugu gugccaggcc cugugccag    89

<210> SEQ ID NO 60
<211> LENGTH: 80
<212> TYPE: RNA
<213> ORGANISM: Homo sapiens

<400> SEQUENCE: 60
ugggaugagg uaguagguug uauaguuuua gggucacacc caccacuggg agauaacuau    60
acaaucuacu gucuuuccua    80

<210> SEQ ID NO 61
<211> LENGTH: 72
<212> TYPE: RNA
<213> ORGANISM: Homo sapiens

<400> SEQUENCE: 61
agguugaggu aguagguugu auaguuuaga auuacaucaa gggagauaac uguacagccu    60
ccuagcuuuc cu    72

<210> SEQ ID NO 62
<211> LENGTH: 74
<212> TYPE: RNA
<213> ORGANISM: Homo sapiens

<400> SEQUENCE: 62
gggugaggua guagguugua uaguuugggg cucugcccug cuaugggaua acauacaauu    60
cuacugucuu uccu    74